United States Patent
Eberhard et al.

(10) Patent No.: US 7,742,796 B2
(45) Date of Patent: Jun. 22, 2010

(54) BREAST IMMOBILIZATION DEVICE AND METHOD OF IMAGING THE BREAST

(75) Inventors: Jeffrey Wayne Eberhard, Albany, NY (US); Abdulrahman Abdallah Al-khalidy, Niskayuna, NY (US); Cynthia Elizabeth Landberg, Clifton Park, NY (US); Bernhard Erich Hermann Claus, Niskayuna, NY (US); Reinhold Franz Wirth, Chandler, AZ (US)

(73) Assignee: General Electric Company, Niskayuna, NY (US)

( * ) Notice: Subject to any disclaimer, the term of this patent is extended or adjusted under 35 U.S.C. 154(b) by 795 days.

(21) Appl. No.: 11/257,901

(22) Filed: Oct. 25, 2005

(65) Prior Publication Data

US 2007/0092059 A1    Apr. 26, 2007

(51) Int. Cl.
*A61B 5/05* (2006.01)
*A61B 6/00* (2006.01)
*A61B 6/04* (2006.01)

(52) U.S. Cl. .................. 600/407; 600/437; 378/37

(58) Field of Classification Search .......... 600/407, 600/415, 443, 421, 437; 378/37; 382/128; 128/890; 604/74, 346
See application file for complete search history.

(56) References Cited

U.S. PATENT DOCUMENTS

| | | | |
|---|---|---|---|
| 3,556,081 A | 1/1971 | Jones | |
| 4,130,112 A * | 12/1978 | Frazer | 600/448 |
| 4,338,948 A * | 7/1982 | Perez-Mendez et al. | 600/437 |
| 5,930,330 A | 7/1999 | Wolfe et al. | 378/98.2 |
| 6,146,377 A * | 11/2000 | Lee et al. | 606/13 |
| 6,298,114 B1 * | 10/2001 | Yoda | 378/37 |
| 6,304,770 B1 * | 10/2001 | Lee et al. | 600/427 |
| 6,418,188 B1 * | 7/2002 | Broadnax | 378/37 |
| 6,480,565 B1 | 11/2002 | Ning | 378/37 |
| 6,587,578 B2 | 7/2003 | Godik et al. | 382/128 |
| 6,682,484 B1 * | 1/2004 | Entrekin et al. | 600/437 |
| 6,786,868 B2 | 9/2004 | Stotzka et al. | |
| 6,883,194 B2 * | 4/2005 | Corbeil et al. | 5/601 |
| 7,188,998 B2 * | 3/2007 | Gregerson et al. | 378/197 |
| 2004/0073106 A1 * | 4/2004 | Lee et al. | 600/415 |
| 2004/0215101 A1 | 10/2004 | Rioux et al. | 600/562 |
| 2005/0113683 A1 | 5/2005 | Lokhandwalla et al. | 600/427 |

FOREIGN PATENT DOCUMENTS

| | | |
|---|---|---|
| DE | 4037387 A1 | 5/1992 |
| DE | 10050232 A1 | 5/2002 |
| JP | 2005363157 A | 6/2007 |

* cited by examiner

*Primary Examiner*—Eric F Winakur
*Assistant Examiner*—Katherine L Fernandez
(74) *Attorney, Agent, or Firm*—Patrick K. Patnode (57) ABSTRACT

A method for imaging a breast is provided. The method includes positioning a breast within a breast holder including a flexible membrane and creating at least a partial vacuum within the flexible membrane. A method of upgrading a mammography system and various configurations of breast holders are also provided.

17 Claims, 9 Drawing Sheets

BREAST IMMOBILIZATION DEVICE AND METHOD OF IMAGING THE BREAST

The invention relates generally to mammography, and more particularly to a breast immobilization device.

In traditional mammography, compression of the breast may be necessary in order to even out the breast thickness so that all of the tissue can be visualized and to spread out the tissue so that small abnormalities are not obscured by overlying breast tissue. In addition, compression allows the use of a lower X-ray dose since a thinner amount of breast tissue is being imaged, while also holding the breast still in order to eliminate blurring of the image caused by motion. Furthermore, compression reduces X-ray scatter to increase sharpness of picture.

In 3D imaging of the breast, the need for compression to spread out tissue so that overlying breast tissue does not obscure small abnormalities, is substantially reduced or effectively eliminated. Similarly, dose management can be addressed by changing the X-ray technique. However, breast compression may still be necessary to immobilize breast tissue during examination to reduce patient motion artifacts and to assure good positioning of the breast tissue. However, the force used for compression and for flattening the breast, increases patient discomfort and potentially reduces patient compliance with recommended breast screening intervals.

Thus, there is a need for a system and method for breast imaging that is comfortable for the patient, allows maximum coverage of the breast tissue during examination, and facilitates immobilization of the breast during examination.

SUMMARY

In accordance with one aspect of the present technique, A method for imaging a breast is provided. The method includes positioning a breast within a breast holder including a flexible membrane and creating at least a partial vacuum within the flexible membrane.

In accordance with another aspect, a method of upgrading a mammography system is provided. The method includes removing at least one breast support structure in a mammography system and positioning a breast holder within the 3D mammography system where the at least one support structure for breast has been removed.

In accordance with yet another aspect, a breast imaging system is provided. The imaging system includes an imaging source that provides an imaging beam, a breast holder for conforming and immobilizing the breast within the breast holder. The breast holder is coupled to a vacuum pump for generating a partial vacuum between the breast and the breast holder. A detector that detects the imaging beam passing through the breast and a positioning unit for positioning the imaging source and the detecting unit, are also included. The positioning unit aligns the imaging source, the breast holder, and the detector in the same axial line.

These and other advantages and features will be more readily understood from the following detailed description of preferred embodiments of the invention that is provided in connection with the accompanying drawings.

DETAILED DESCRIPTION OF EXEMPLARY EMBODIMENTS

In the subsequent paragraphs, an apparatus for imaging the breast of a subject will be explained in detail. The apparatus described hereinafter provides a means for immobilizing breast tissue during the exam to manage patient motion artifacts and also assures good positioning to enable good coverage of breast tissue. Furthermore, the apparatus reduces the force used for compression and eliminates flattening of the breast, thereby increasing the comfort of the subject and potentially improve compliance of the subject with recommended breast screening intervals. As will be appreciated by those of ordinary skill in the art, the present techniques are applicable to other imaging systems besides X-ray or tomosynthesis, for example ultrasound scanning techniques. Indeed, the exemplary uses and implementations described herein are merely provided as examples to facilitate understanding of the presently contemplated techniques. Therefore, the various aspects of the present technique will be explained, by way of example only, with the aid of figures hereinafter.

Figure 1:
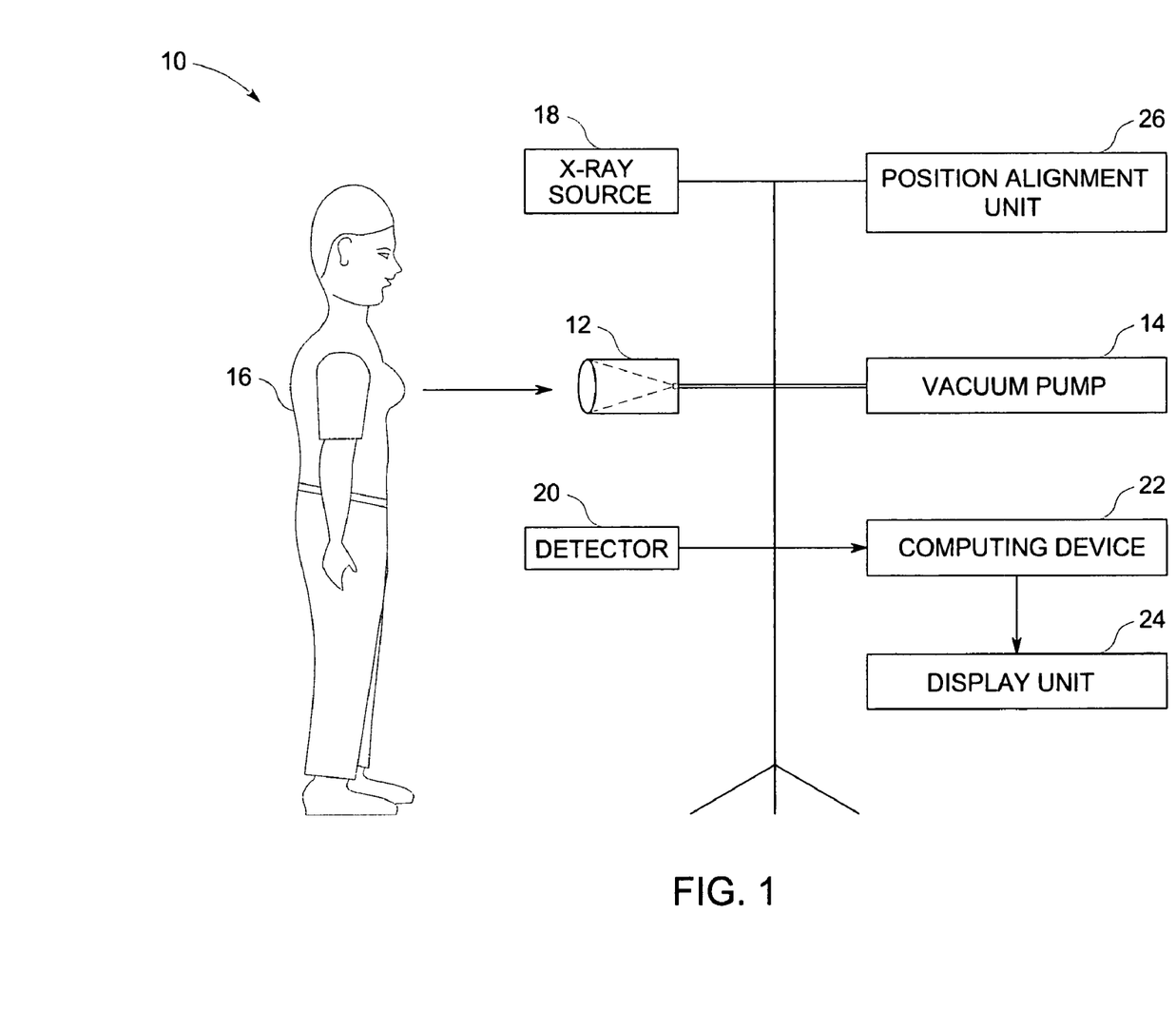
FIG. 1 is a diagrammatical view of a breast imaging system in accordance with aspects of the present technique.

Referring generally to FIG. 1, a breast holder will be described by reference to an exemplary breast imaging system designated generally by numeral 10. It should be appreciated, however, that the breast holder may find application in a range of settings and systems, and that its use in the breast imaging system shown is but one such application. The breast imaging system 10 includes a breast holder 12, which is coupled to a vacuum pump 14. The breast holder 12 is a closed enclosure that includes a membrane that can hold the breast of a subject 16 so that there are no motion artifacts arising out of unwanted movement of breast tissue.

The exemplary breast imaging system 10 also includes an X-ray source 18 and a detector 20. The X-ray source, or any other imaging beam source known to those of ordinary skill in the art, generates an imaging beam that is detected by the detector 20. Detector 20 may be coupled to a computing device 22 that analyses the data acquired by the detector and generates an image of the imaged volume, for example, the breast tissue. This generated image may be displayed on a display unit 24. A position alignment unit 26, which may be coupled to the computing device 22, aligns the position of the X-ray source 18 and/or detector 20 for proper imaging of the tissue. Furthermore, the breast holder 12 may be either attached to the position alignment unit 26, through a rigid or flexible coupling, or placed on a breast support, depending on the application. For example, in tomosynthesis, the breast support may preferably be the surface of the detector 20, while in computed tomography (CT), it may preferably be a separate device, positioned intermediate in position between the X-ray source 18 and the detector 20.

Figure 2:
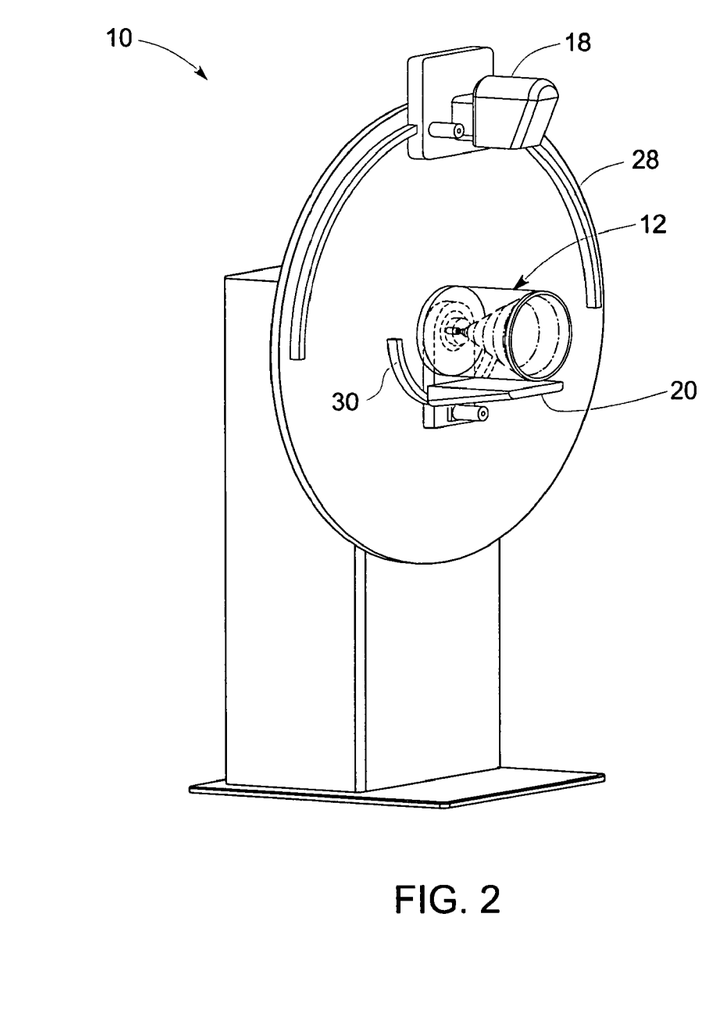
FIG. 2 is a perspective view of the breast imaging system in accordance with aspects of the present technique.

FIG. 2 is a perspective view of one embodiment of the exemplary breast imaging system 10 of FIG. 1. As previously described, the breast imaging system 10 includes a breast holder 12. An imaging beam source 18, such as an X-ray source, may be mounted on a source bearing rail 28, while a detector 20 may be mounted on a detector bearing rail 30. The source bearing rail 28 and the detector bearing rail 30 may be utilized to guide the source 18 and detector 20 and align them such that desired imaging of the breast tissue may be achieved. It may be noted that the alignment of source 18 and detector 20, may be automated or manually controlled. In automated control, motors may drive the beam source 18 and/or the detector 20 along the respective bearing rails 28 and 30.

Figure 3:
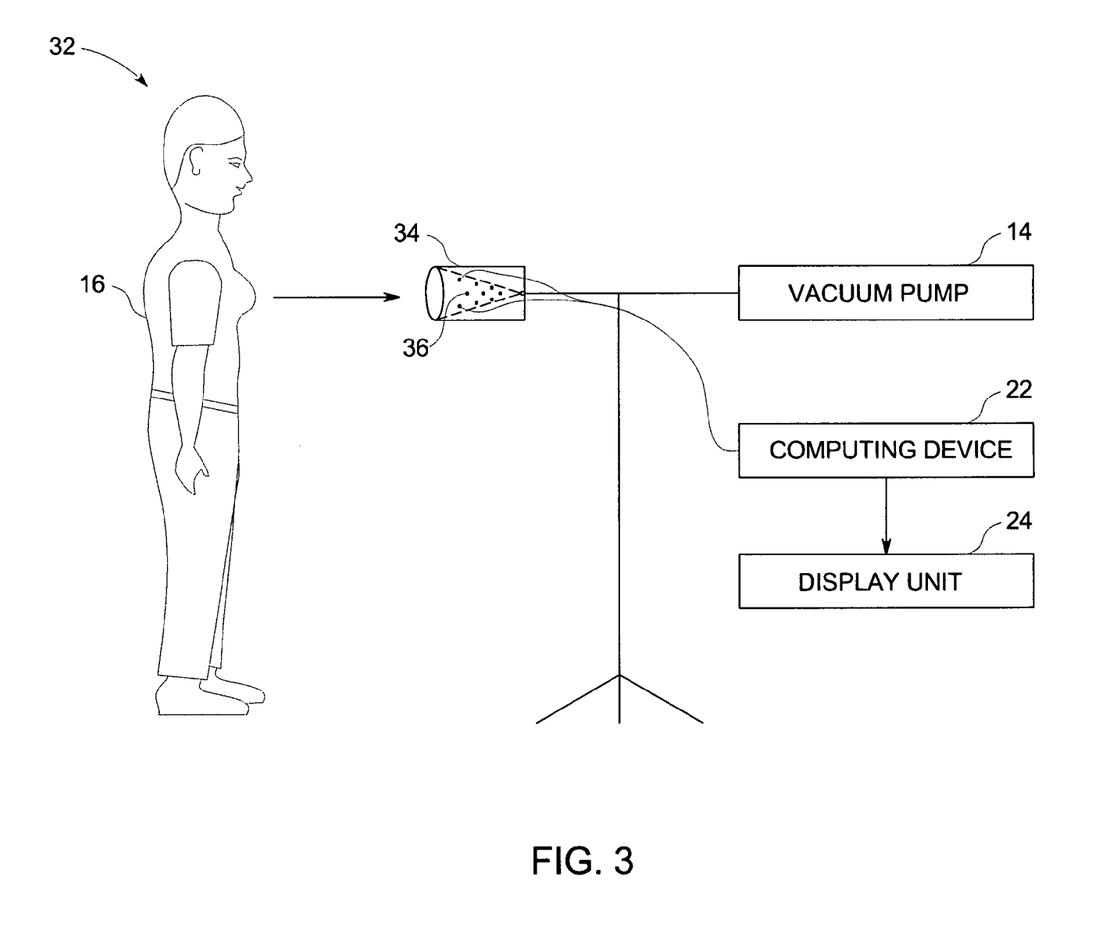
FIG. 3 is a diagrammatical view of an ultrasound breast imaging system in accordance with aspects of the present technique.

Referring now to FIG. 3, a diagrammatical view of an ultrasound breast imaging system 32 is illustrated. The ultrasound breast imaging system 32 includes an ultrasound breast holder 34 that is coupled to a vacuum pump 14. The ultrasound breast holder 34 includes a membrane, which supports and immobilizes the breast of a subject 16. The membrane of the ultrasound breast holder 34 includes ultrasound transducers 36 that allow scanning of the breast tissue via ultrasound techniques. A computing device 22 controls the ultrasound signals that is generated and received by the ultrasound transducers 36. The received ultrasound signals may be analyzed for generating an image of the breast tissue, for determining any lesions, tumors, or other tissue growth in the breast of the subject. The generated image may be displayed on a display unit 24, which may include a computer monitor, a liquid crystal display (LCD) screen, or the like.

Figure 4:
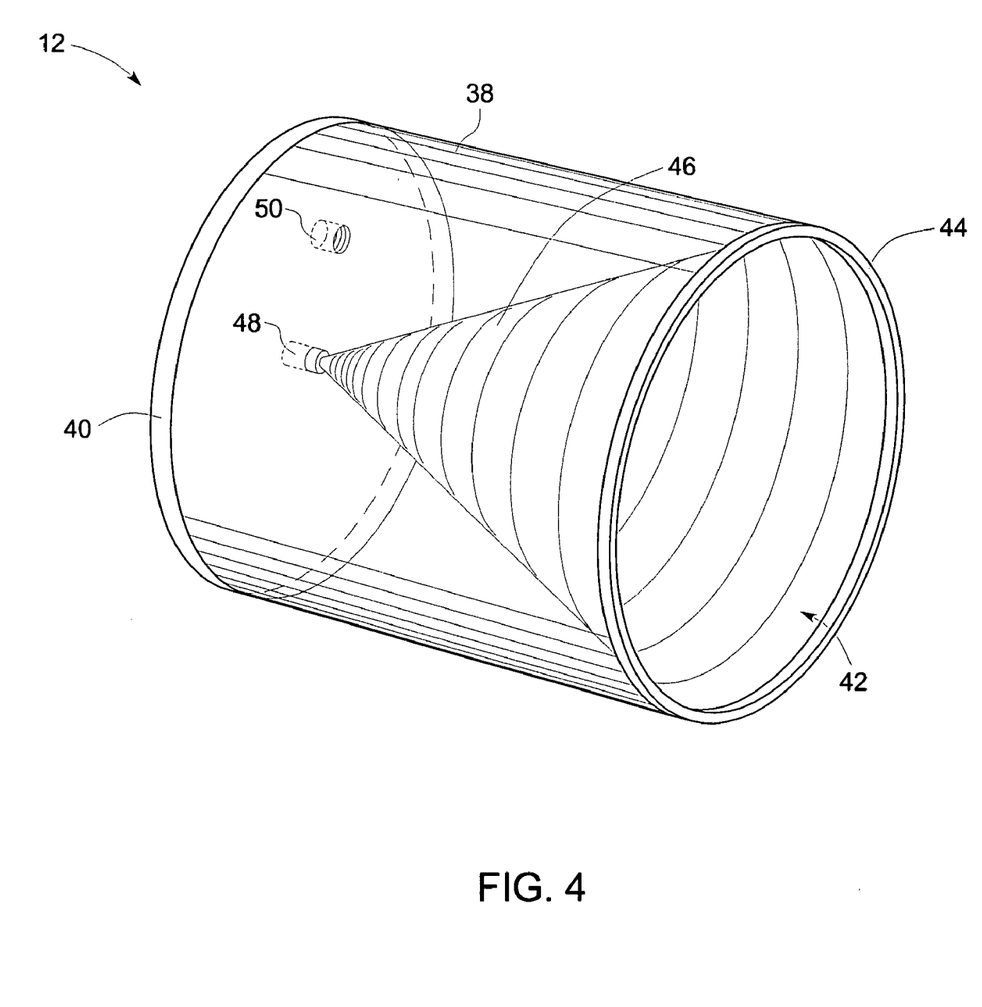
FIG. 4 is a perspective view of one embodiment of the breast imaging holder in accordance with aspects of the present technique.

FIG. 4 is a perspective view of an embodiment of a breast holder 12. The depicted breast holder 12 includes an outer shell or an outer body 38, a base plate 40, and an open end 42. The outer body 38 of the breast holder 12 may be made of a pliable material, such as plastic, that allows X-ray signals to penetrate into the breast holder. On the rim 44 of the open end 42, is attached a membrane 46, which is in a conical shape with the vertex of the conical membrane being coupled to a hole 48. The membrane 46 may be made of synthetic rubber, or other material that is comfortable for the subject and flexible enough so that the membrane attains the shape of the breast. The membrane 46 may be sealingly coupled to the rim 44 of the open end 42 and the hole 48 such that these two ends are open. At the hole 48, a vacuum pump 14 may be sealingly coupled so that the volume defined by the membrane 46 may be fully or partially evacuated during operation. Optionally, the base plate 40 of the breast holder 12 may be provided with a hole 50 for allowing air to escape as the breast holder 12 is partially filled with tissue when vacuum pressure is applied inside the membrane 46. A sealing liquid or cream may be applied to the patient contact surface on the chest wall to improve sealing and ability of the vacuum to draw the tissue into the breast holder 12.

In operation, the breast of a subject is positioned inside the membrane 46 from the open end 42, so that the membrane assumes the shape of the breast. Air present within the membrane 46 may be evacuated to a partial vacuum pressure. Under partial vacuum, the breast is drawn into the breast holder 12 and tissue is effectively pulled from near the chest wall into the breast holder. The degree of evacuation may be adjusted to achieve appropriate compromise between comfort of the subject and tissue drawn into the breast holder 12. Because the breast tissue is drawn into the breast holder 12, good coverage of the tissue is achieved.

Figure 5:
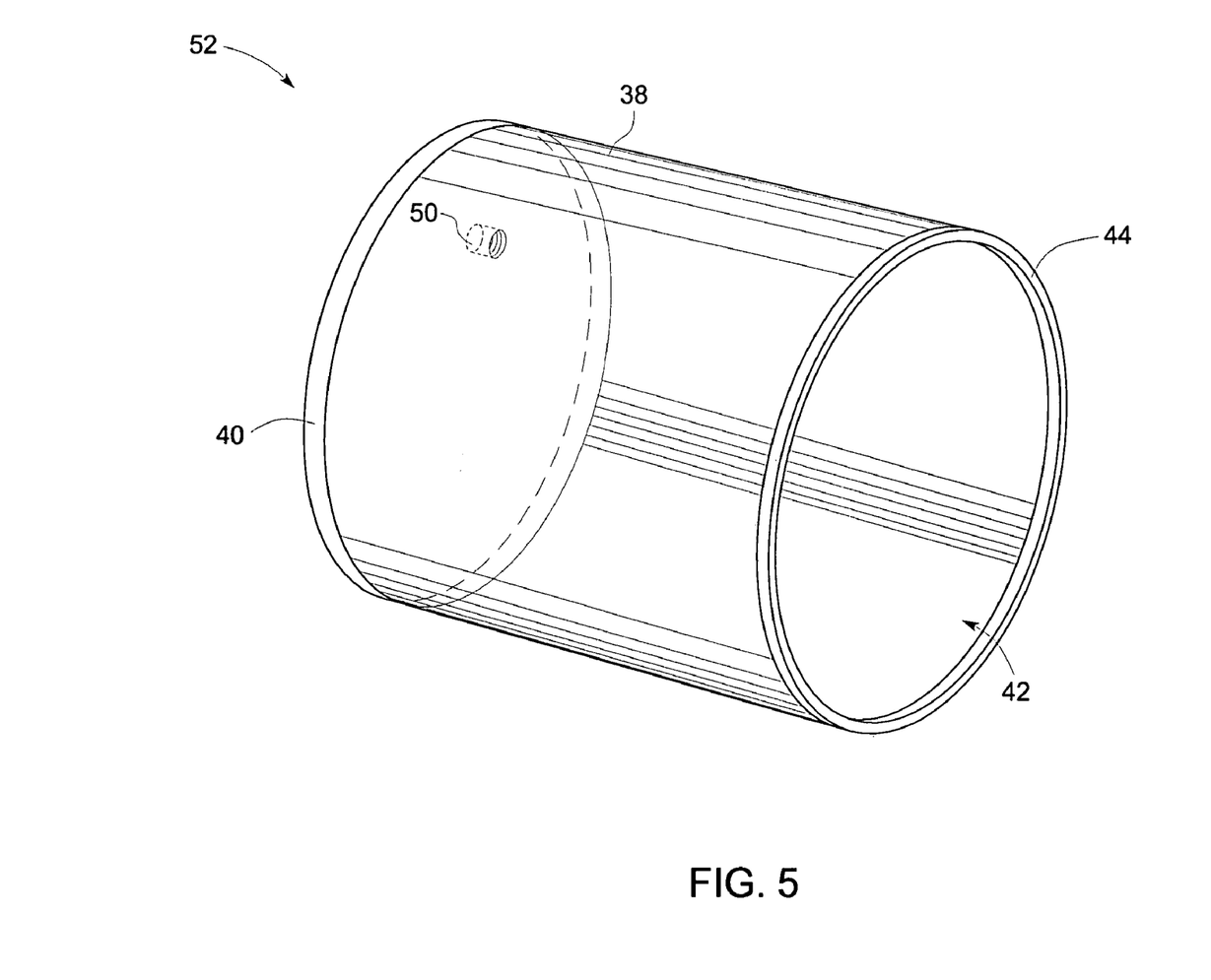
FIG. 5 is a perspective view of an alternative embodiment of the breast imaging holder in accordance with aspects of the present technique.

Turning now to FIG. 5, an alternative embodiment of the breast holder 52, without a membrane is illustrated. In operation, the breast holder 52 may be filled with a fluid medium that fills the space between the breast and the outer body 38. Hole 50 may be used to fill the breast holder 52 with the fluid medium, after positioning the breast. Alternatively, the breast holder 52 may be pre-filled with the fluid medium, and the fluid may be drawn out of the hole 50.

Figure 6:
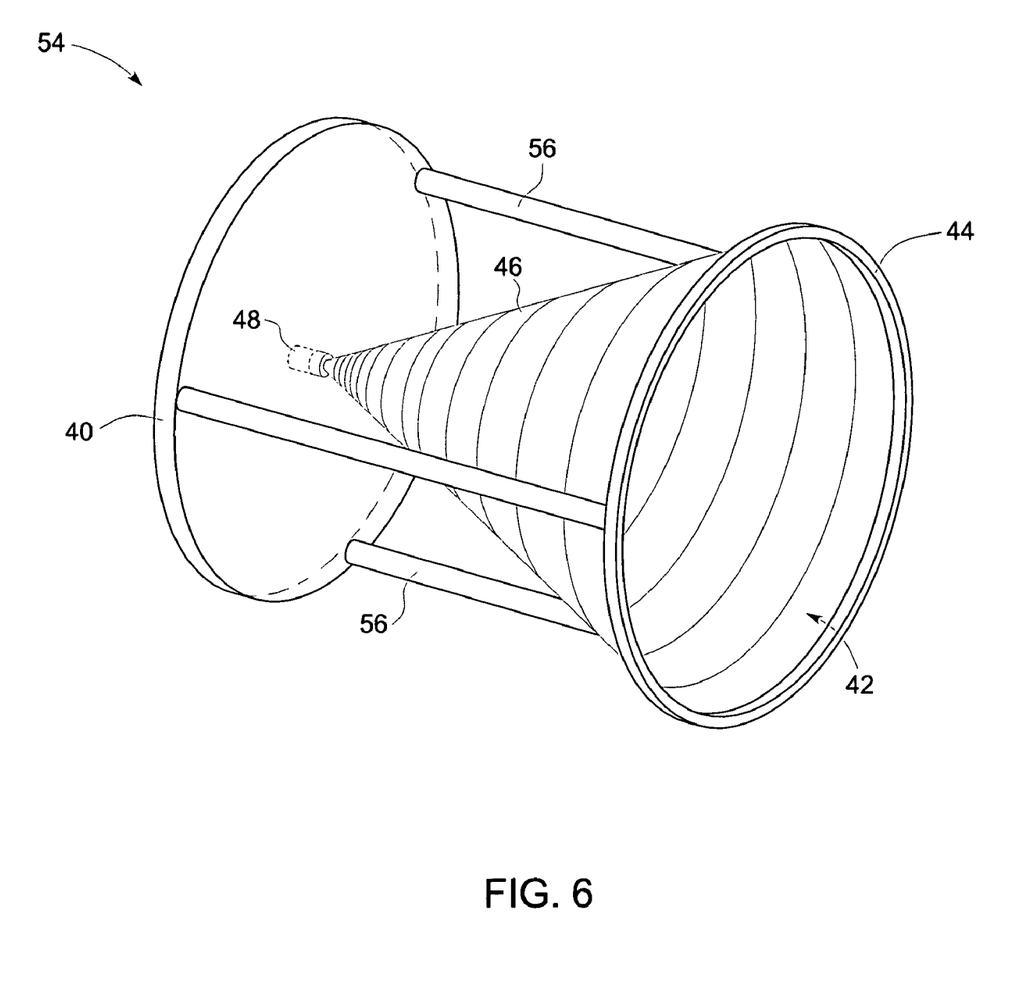
FIG. 6 is a perspective view of yet another embodiment of the breast imaging holder in accordance with aspects of the present technique.

Another alternative embodiment of the breast holder is illustrated in FIG. 6. In this embodiment, the breast holder 54 has a rim 44 on which is attached the membrane 46. However, this breast holder 54 does not have an outer body. Instead, the breast holder 54 includes one or more support structures 56 that provide mechanical support to the rim 44. The membrane 46 may be coupled to the rim 44 and a hole 48 provided on the base plate 40. This breast holder 54 may be used similarly as the other configurations discussed above.

Figure 7:
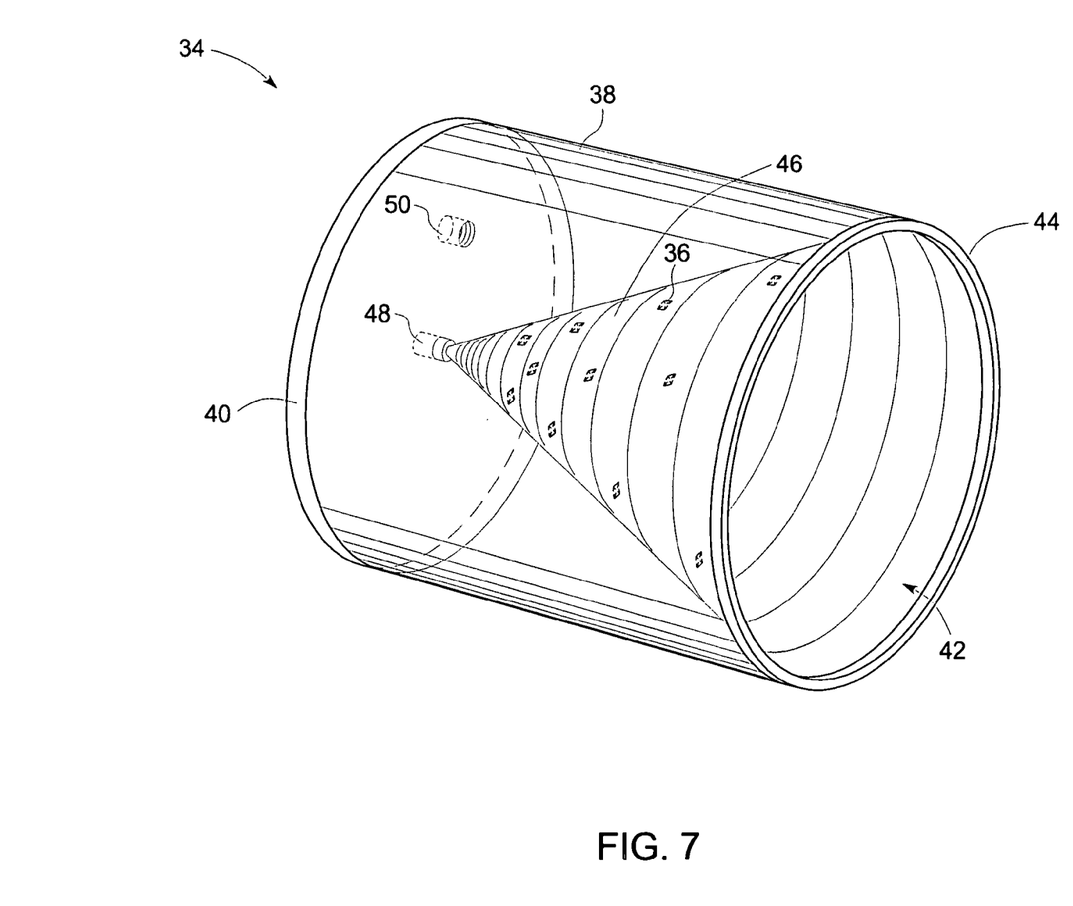
FIG. 7 is a perspective view of an embodiment of the breast imaging holder for use in an ultrasound breast imaging system in accordance with aspects of the present technique.

FIG. 7 is a perspective view of an embodiment of the breast holder for use in the ultrasound breast imaging system of FIG. 3. The breast holder 34 is similar to the breast holder 12, shown in FIG. 4. However, in this embodiment, the membrane 46 includes ultrasound transducers 36 that may be embedded on the membrane 46. In other embodiments, the ultrasonic transducers 36 may be positioned on the outer shell 38, while the space between the outer shell and the membrane 46 is filled with a liquid (e.g. water) to allow the ultrasound to propagate into the breast. The ultrasound transducers 36 may transmit and receive acoustic signals for an ultrasound scan of the breast. As noted above, during an ultrasound scan, the membrane 36 and/or the space between the membrane and the outer body 38 may be filled with a fluid medium, such as water for facilitating the scan by allowing acoustic waves to penetrate easily.

Figure 8:
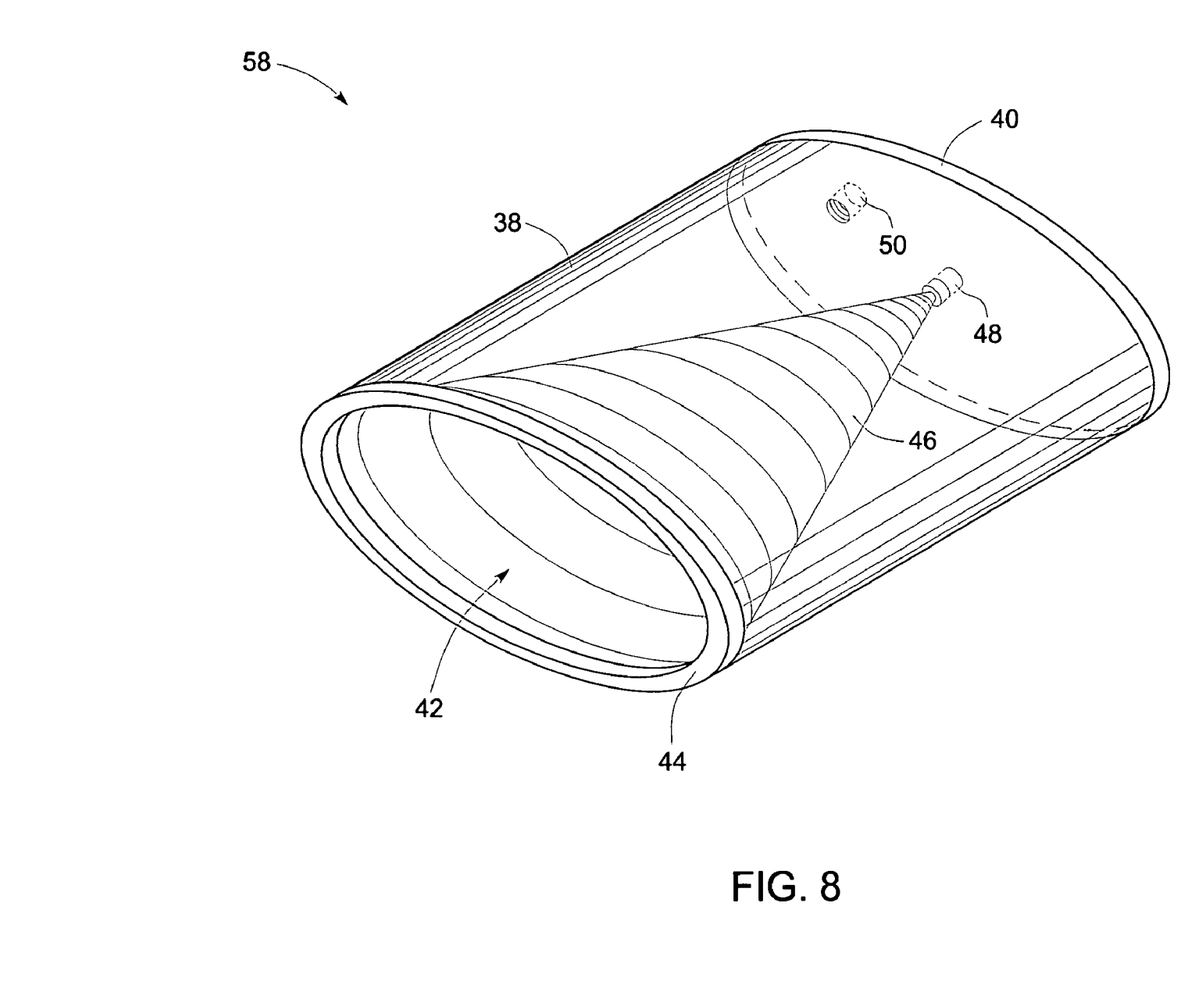
FIG. 8 is a perspective view of an embodiment of an elliptical breast imaging holder in accordance with aspects of the present technique.
Figure 9:
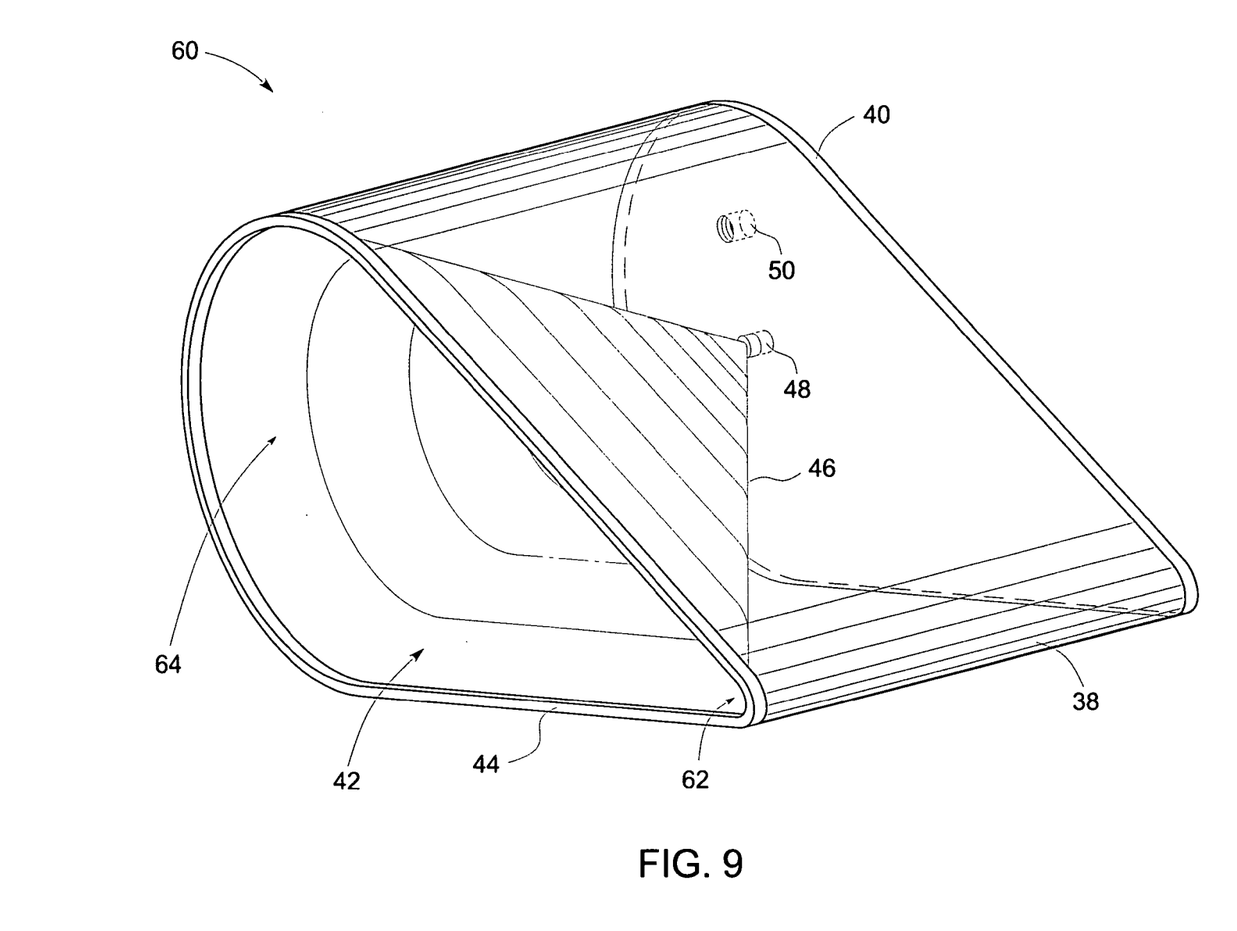
FIG. 9 is a perspective view of another embodiment of a breast imaging holder in accordance with aspects of the present technique.

Various other configurations of the breast holder may be designed, depending on patient characteristics, system requirements, among other parameters. Breast holders of various sizes (e.g., diameter, holder body height) may be provided to allow for patient specific anatomical differences. Although, the described embodiments have a cylindrical shape and circular cross-section, other embodiments may have an elliptical configuration or a hexagonal configuration or more complex shapes. Elliptical cross-sections, as illustrated in FIG. 8, and sections with a secondary aperture to allow better inclusion of tissue near the pectoral muscle, as illustrated in FIG. 9 may be constructed. In the elliptical configuration 58, the base plate 40 and the rim 44 may be designed in an elliptical shape. Similarly, in the configuration 60 of FIG. 9, the base plate 40 and the rim 44 may be designed such that a sectional plane for the same would have a narrow end 62 and a broad end 64, as illustrated. The narrow end 62 allows inclusion of the pectoral muscle of the subject for providing better scanning coverage.

In all the configurations discussed above, outer body 38 may be made of a plastic or other rigid material that transmits X-rays. Alternatively, a more pliable material that can more easily conform to the shape of the anatomy may be utilized. The membrane 46 may be made of a soft, pliable material, such as a synthetic rubber compound or other material approved by Food and Drug Administration (FDA). Custom fabrications, where the patient is fitted a few hours or days before the breast examination, may also be implemented.

Although the embodiments illustrated and described hereinabove represent only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. For example, an existing breast support structure (such as, a breast compression paddle) in a breast X-ray imaging system, a breast CT scanning system, a tomosynthesis application, or a breast ultrasound imaging system, may be replaced with the breast holder that is disclosed hereinabove. Furthermore, breast holders described above may be employed in the applications noted above as will be appreciated by those of ordinary skill in the art. Similarly, the breast holder may have other cross-sections, such as a hexagonal configuration.

Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A method of upgrading a mammography system, comprising:
   removing at least one breast support structure from a mammography system; and
   replacing the removed breast support structure with a breast holder,
   wherein the breast support structure comprises a breast compression paddle, a breast stand, or both, wherein the breast holder comprises a base plate, a ring-shaped rim coupled to the base plate, and a flexible membrane having a substantially continuous surface, and wherein the flexible membrane is coupled to the base plate and the rim, the flexible membrane comprising a substantially open end, and a substantially closed end coupled to an opening in the base plate.

2. The method of claim 1, further comprising positioning the breast holder between an imaging source and an imaging detector in the mammography system.

3. The method of claim 1, wherein the breast holder comprises an outer shell coupled to the base plate and the rim such that the outer shell, the base plate and the rim together form a covered structure.

4. The method of claim 1, wherein the opening in the base plate allows fluid flow into and out of the breast holder when a breast is positioned within the breast holder.

5. The method of claim 1, wherein the rim is coupled to the base plate via support structures.

6. A breast imaging system, comprising:
   an imaging source configured to provide an imaging beam;
   a breast holder configured to conform to and immobilize the breast within the breast holder, wherein the breast holder is coupled to a vacuum pump for generating a partial vacuum between the breast and the breast holder, wherein the breast holder comprises a base plate, a ring-shaped rim coupled to the base plate via support structures, and a flexible membrane having a substantially continuous surface, and wherein the flexible membrane is coupled to the base plate and the rim, the flexible membrane comprising a substantially open end, and a substantially closed end coupled to an opening in the base plate;
   a detector configured to detect the imaging beam that passes through the breast; and
   a positioning unit configured to position the imaging source and the detector such that the imaging source, the breast holder, and the detector are in the same axial line.

7. The breast imaging system of claim 6, wherein the imaging source comprises an X-ray imaging source.

8. The breast imaging system of claim 6, wherein the detector comprises an X-ray detector.

9. The breast imaging system of claim 6, wherein the imaging source comprises an ultrasound imaging source.

10. The breast imaging system of claim 6, wherein the detector comprises an ultrasound detector.

11. A breast holder, comprising:
    an outer shell;
    a base plate coupled to the outer shell;
    a ring-shaped rim coupled to the outer shell, such that the outer shell, the base plate and the rim together form a covered structure; and
    a flexible membrane having a substantially continuous surface, wherein the flexible membrane is coupled to a first opening, provided in the base plate, and the rim.

12. The breast holder of claim 11, the outer shell comprising a plastic material.

13. The breast holder of claim 11, the flexible membrane comprising a pliable material that can conform to the shape of the breast.

14. The breast holder of claim 11, the base plate comprising a second opening for allowing the passage of fluids.

15. The breast holder of claim 11, wherein the breast holder is coupled to a vacuum pump at the first opening for drawing air out of the flexible membrane during imaging.

16. A breast holder, comprising:
    an outer shell;
    a base plate coupled to the outer shell;
    a ring-shaped rim coupled to the outer shell, such that the outer shell, the base plate and the rim together form a covered structure; and
    a flexible membrane having a substantially continuous surface, wherein the flexible membrane is coupled to the base plate and the rim, the flexible membrane comprising a substantially open end and a substantially closed end coupled to an opening in the base plate, and wherein the opening facilitates fluid flow into and out of the flexible membrane when a breast is positioned within the flexible membrane.

17. A breast holder, comprising:
    a base plate;
    a ring-shaped rim coupled to the base plate via support structures; and
    a flexible membrane having a substantially continuous surface, wherein the flexible membrane is coupled to the base plate and the rim, the flexible membrane comprising a substantially open end, and a substantially closed end coupled to an opening in the base plate, wherein the opening facilitates fluid flow into and out of the flexible membrane when a breast is positioned within the flexible membrane.

* * * * *